United States Patent [19]

Fery

[11] 4,352,674

[45] Oct. 5, 1982

[54] METHOD OF TRACING A WELL DRILLING MUD

[75] Inventor: Jean J. Fery, Bar Le Duc, France

[73] Assignee: Compagnie Francaise des Petroles, Paris, France

[21] Appl. No.: 222,843

[22] Filed: Jan. 6, 1981

[30] Foreign Application Priority Data

Jan. 8, 1980 [FR] France ................................ 80 00263

[51] Int. Cl.$^3$ ............................................. G01N 33/24
[52] U.S. Cl. ............................... 23/230 EP; 166/250; 166/254; 175/42; 175/65
[58] Field of Search .................... 23/230 EP; 166/250, 166/254, 255, 252; 175/65, 42, 50

[56] References Cited

U.S. PATENT DOCUMENTS

| | | | |
|---|---|---|---|
| 2,387,513 | 10/1945 | Hocott | 175/50 X |
| 2,868,625 | 1/1959 | Frank | 23/230 EP |
| 3,623,842 | 11/1971 | Deans | 23/230 EP |
| 3,843,524 | 10/1974 | Perricone et al. | 175/65 X |
| 4,168,746 | 9/1979 | Sheely | 23/230 EP X |
| 4,264,329 | 4/1981 | Beckett | 23/230 EP |

*Primary Examiner*—Kenneth M. Schor
*Attorney, Agent, or Firm*—Sughrue, Mion, Zinn, Macpeak & Seas

[57] ABSTRACT

In a method of tracing a well drilling mud by determining the concentration of a tracer ion in samples of filtrate from a drilling mud which contains a predetermined concentration of the tracer ion, the improvement wherein the tracer ion is the acetate ion and is present in the drilling mud in a concentration of about $1.10^{-3}$ to about $5.10^{-2}$ ions per liter.

7 Claims, No Drawings

METHOD OF TRACING A WELL DRILLING MUD

FIELD OF THE INVENTION AND DESCRIPTION THEREOF

This invention is concerned with a method of tracing a well drilling mud for the purpose of complete exploration of the strata penetrated and of the formation liquids produced by a petroleum reservoir.

An investigation of this kind may be necessary, for example, when there are hydrocarbons present which are different from those already detected as a result of another drilling carried out in the same zone or when the water produced has a similar salinity to that of the filtrate from the mud.

Despite the many types of loggings which can be carried out during a drilling, the conditions just mentioned require a rigorous interpretation of such loggings and only a method of tracing which is applicable to the filtrate from a drilling mud is fully effective.

Known tracing methods are of three types, namely the use of dyestuffs, the use of radioactive tracers, and the use of soluble ions.

The use of dyestuffs, such as fluorescein, fuchsine and the like, has the major disadvantage that it can only provide valid quantitative results by spectrophotometric determination.

Radioactive tracers require particular precautions and can lead to interactions with the logging measurements, in particular if the logging is carried out by means of gamma rays.

Tracers consisting of soluble ions which are not encountered in the waters present in the formations drilled have the advantages that they can be determined by ordinary chemical procedures, that is without the use of spectrophotometry or other complex methods, and they do not interfere with logging measurements obtained by gamma irradiation.

Numerous tracers of this kind have already been tested, for example dichromate, chromate, nitrate, ammonium, cobalt, nickel, manganese, vanadium and lithium, but these ions either have some degree of instability or are incompatible with the drilling medium, and they have not proved satisfactory to the operators, either because of the disappearance of the ion or because of the complexity of the method of determination required which can necessitate the presence of an experienced chemist and/or the use of equipment which is complex or too sensitive to be usable on site.

Despite the desirability of finding a simple and practical method using a tracer ion which gives reliable quantitative results, and the considerable experimentation which has been carried out to this end, no such method has yet been found which meets these requirements when used under the following conditions:

temperature increase of at least 150° C., use with the most varied types of drilling muds, use in the presence of fresh water or seawater, and use in the presence of any of the following conventional products: lignosulphates of iron and chromium, sodium hydroxide, bentonite, attapulgite, polymers which are commercially available under the names "Flocgel", "Drispac", "Rhodopol" and CMC, i.e. carboxymethylcellulose, iron hydroxide and diesel oil.

We have now surprisingly found, however, that the use of the acetate ion in a particular range of concentrations as a tracer ion in drilling muds enables reliable quantitative results to be simply obtained.

According to the present invention, therefore, there is provided a method of tracing a well drilling mud by determining the concentration of a tracer ion in samples of filtrate from a drilling mud which contains a predetermined concentration of the tracer ion, in which the tracer ion is the acetate ion, $CH_3COO^-$, and is present in the drilling mud in a concentration of from $1.10^{-3}$ to $5.10^{-2}$ ions per liter.

The effectiveness of the acetate ion for this purpose is surprising because previous experimentation had shown that the acetate ion inhibits the swelling of calcium montmorillonite clay, although the inhibiting effect is substantially reduced at concentrations above about 0.5 mol per liter. We have found, on the contrary, that whatever the products present in the drilling mud, the use of acetate ion in the range of concentrations mentioned does not affect the characteristics, in particular the swelling properties, of the clay used in the drilling mud so that any risk of instability of the walls of the drill hole or of redispersion of the recycled clay particles is avoided.

The acetate ion concentration in the filtrate sample is preferably determined by treating the latter with a strong acid, such as dilute hydrochloric or sulphuric acid, and distilling the acetic acid thereby liberated at a temperature of from 105° to 130° C.

Extraneous weak acids, that is weak acids other than acetic acid and, in particular sulphurous acid, may be present in the distillate, particularly when lignosulphonates are present in the drilling mud, and these are preferably converted into strong acids by oxidation with iodine prior to determining the overall strong acidity, that is, acidity due to strong acids, and the acetic acid.

Further features and characteristics of the invention will become apparent from the following detailed description of preferred embodiments of the method.

The acetate ion may be added to the drilling mud in the form of any of its water-soluble salts; silver acetate and mercurous acetate are not suitable as they are only sparingly soluble. It is preferred to use sodium acetate trihydrate. We have found that none of the complexes which can be formed with acetate ions interferes with the tracing method.

The drilling mud is prepared by adding sodium acetate or other acetate salt thereto so as to obtain a mixture which preferably has before injection into the well and in circulation, an acetate concentration of about 0.03 to 0.05 ion per liter.

By way of example, it will be assumed that the chosen concentration is 0.04 ion per liter in the case of crystalline sodium acetate.

The sample of the drilling mud is taken at the desired drilling level and 100 cm³, for example, of the filtrate from the mud sample collected is poured into a distillation vessel. The acetic acid is released by means of sulphuric acid, for example by introducing 2 cm³ and 5 N sulphuric acid.

Depending on the products present into the mud, the reaction $CH_3COONa + H_2SO_4 \rightarrow CH_3COOH + NaHSO_4$ can be accompanied by the formation of extraneous weak acids, in particular when lignosulphonates are present, so that, after distillation at from 105° to 130° C., the distillate collected after passage through the condenser can contain bisulphites. The distillate is collected in a measuring vessel containing, for example, 100 cm³ of distilled water.

The bisulphites are then oxidised with iodine by adding a sufficient volume of a 0.1 N iodine solution to cause the brown colour of iodine to appear, indicating the complete conversion of the bisulphites to bisulphates: $I_2 + 2H_2O + SO_2 \rightarrow H_2SO_4 + 2HI$.

The excess iodine is neutralised with sodium thiosulphate: $2S_2O_3^{2-} + I_2 \rightarrow S_4O_6^{2-} + 2I^-$. The neutralisation is conveniently followed by carrying it out in the presence of starch paste which is decolourised when neutralisation by the thiosulphate is complete.

The overall acidity of the distillate can then be determined by neutralisation with a strong base, such as sodium hydroxide. Any suitable indicator may be used to indicate the neutralisation point. It is preferred to use methyl orange. A few drops of the latter are added before the sodium hydroxide and the methyl orange turns red because of the presence of the strong acid. The volume V of the sodium hydroxide solution added so as to cause the methyl orange to turn from red to orange (pH 4.2 to 4.3) is noted and from it is calculated the strong acidity of the distillate. A few drops of phenolphthalein are then added and a further volume $V_1$ of the sodium hydroxide solution so as to cause the colour to turn to violet-red (pH=8.3), this volume, $V_1$, corresponding to the complete neutralisation of the weak acids from which can be calculated the concentration, C, of crystalline sodium acetate ($CH_3COONa.3H_2O$) per liter. The concentration C is equal to 1.36 ($NV_1$), the molecular weight of crystalline acetate being 136 and N being the normality of the sodium hydroxide solution. If N=0.1, C=0.136($V_1$), $V_1$ being expressed in $cm^3$.

This method of tracing by determining the acetic acid after boiling is effective even in the presence of other acids which may be formed as the latter disappear on boiling or are not entrained during distillation. Thus, carbonic acid decomposes with the disappearance of $CO_2$, which escapes during boiling; $CO_2 + H_2O \rightleftharpoons H_2CO_3$.

Phenol, which is a weak acid which only distils at about 181° C., also does not interfere with the determination carried out in this way.

Hydrogen sulphide, which could be troublesome as a weak acid, is converted into the strong acid HI by the excess iodine: $I_2 + H_2S \rightleftharpoons 2HI + S$ and does not cause difficulties in the determination of the acetic acid.

We have found that complexes formed with acetic acid are of low stability and do not interfere with the determination. By way of example, $Fe^{3+}/CH_3COO_2^-$ is destroyed under the action of heat:

$3Fe^{3+} + 6CH_3COO^- + 2OH^- \rightleftharpoons [Fe_3(CH_3COO)_6 \cdot (OH)_2]^+$.

As a result of numerous experiments, we have determined percentage errors of from 1.5 to 13 in amounts of acetate varying from 0.2000 to 4.000 grams per liter. It will be apparent that if a concentration of sodium acetate of less than 0.5 g/liter is used, the sodium hydroxide solution used should be sufficiently dilute to maintain the precision of the determination.

If the filtrate which it is desired to analyse contains crude oil, it is desirable to effect prior extraction of the oil with carbon tetrachloride or other solvent appropriate to the nature of the crude.

The present invention also comprises a modification of the method of determining acetic acid described above, the modification taking account of the fact that the development of the pH during the course of the determination causes redissociation of strong acids into weak acids; this effect can be suppressed by neutralisation in an oxidising medium.

Furthermore, the uncertainty of the pH of the strong acidity can be limited by making use of the known pK of acetic acid at 4.65. This value is substantially unaffected by the temperature or the medium in which the solution is present.

The modification accordingly comprises effecting oxidation of the extraneous weak acids with iodine and exact neutralisation of the excess iodine, as above described, and then adding an excess of iodine of a known volume $V_2$ and normality $N_1$, partially neutralising the acidity of the distillate with a measured volume $V_3$ of a base of normality N to obtain a pH of 4.65, continuing the neutralisation of the acidity until a pH of 8 is obtained by the addition of a further quantity of the base, the total volume of base used being $V_4$, determining the volume $V_5$ of the final excess of iodine, preferably by the use of a thiosulphate solution of the same normality as that used previously, and then determining the concentration of the tracer ion from the difference between the molar quantity of base contained in the volume ($V_4-V_3$) of base used for the neutralisation of the acidity between pH 4.65 and pH 8 and the molar quantity of iodine contained in the volume of iodine ($V_2-V_5$) used in reoxidation of extraneous weak acids generated by the variation of the pH during the determination.

The concentration, $C_1$, in grams per liter, of crystalline sodium acetate, $CH_3COO\ Na.3H_2O$, is therefore given, for a monovalent base, such as sodium hydroxide, and for a volume $V_6$ of distillate, as determined by this procedure by the formula:

$$C_1 = \frac{N(V_4 - V_3) - N_1(V_2 - V_5)}{V_6} \times 272$$

For other acetate salts, 272 should, of course, be replaced by the molecular weights of such other salts.

I claim:

1. A method of tracing a well drilling mud by determining the concentration of a tracer ion in samples of filtrate from a drilling mud which contains a predetermined concentration of the tracer ion, wherein the tracer ion is the acetate ion, $CH_3COO^-$, and is present in the drilling mud in a concentration of from about $1 \times 10^{-3}$ to about $5 \times 10^{-2}$ ions per liter; said method comprising:

providing said filtrate from a drilling mud which contains said tracer ion; determining the acetate ion concentration in the filtrate sample by treating said filtrate with a solution of a strong acid selected from the group consisting of hydrochloric acid and sulphuric acid and distilling the acetic acid thereby liberated at a temperature of from about 105° to about 130° C.; and determining the strong acidity of the distillate by adding thereto an N solution of a strong base until the pH of the resulting solution is indicated by an indicator to be about 4.2-4.3, and then determining the weak acidity representing the tracer ion concentration by adding a volume $V_1$ of a base solution until the pH of the resulting solution is indicated by an indicator to be about 8.3.

2. A method as set forth in claim 1, wherein extraneous weak acids present in the distillate are oxidised to strong acids by treatment of said distillate with an iodine solution prior to the determination of the acetic acid.

3. A method as set forth in claim 2, wherein prior to the first addition of a strong base, methyl orange is added to the distillate, and wherein the strong acidity of the distillate is determined by adding thereto an 0.025 N solution of a strong base until methyl orange, present as an indicator, turns from red to orange, then adding phenolphthalein to the resulting solution, and the weak acidity representing the tracer ion concentration is then determined by adding a volume $V_1$ of the base solution until phenolphthalein, present as an indicator, turns violet-red.

4. A method as set forth in claim 1, wherein extraneous weak acids present in the distillate are oxidised to strong acids with an excess of an iodine solution, the excess of iodine is exactly neutralised, an excess of an iodine solution of a known volume $V_2$ and normality $N_1$ is added, the acidity of the distillate is partially neutralised with a measured volume $V_3$ of a base of normality N to obtain a pH of 4.65, the neutralisation of the acidity is continued to a pH of 8 by the addition of a further quantity of the base, the total volume of base used being $V_4$, the volume $V_5$ of the final excess of iodine is determined, and the concentration of the tracer ion is determined from the difference between the molar quantity of base contained in the volume ($V_4$-$V_3$) of base used for the neutralisation of the acidity between pH 4.65 and pH 8 and the molar quantity of iodine contained in the volume of iodine ($V_2$-$V_5$) used in reoxidation of extraneous weak acids generated by the variation of the pH during the determination.

5. A method as set forth in claim 1, wherein acetate ion is added to the drilling mud in the form of sodium acetate trihydrate.

6. The method of claim 1, wherein the pH of the distillate after the first addition of said strong base is determined by adding an indicator exhibiting a change in color at a pH of about 4.2-4.3 prior to the first addition of said strong base, and the pH of the distillate solution after said second addition of strong base is determined by adding a second indicator exhibiting a color change at a pH of about 8.3 prior to the second addition of said base, and ending addition of the base when the color change of the indicators is observed.

7. The method of claim 6, wherein said first indicator is methyl orange, and said second indicator is phenolphthalein.

* * * * *